US012291748B2

(12) United States Patent
Chen et al.

(10) Patent No.: US 12,291,748 B2
(45) Date of Patent: May 6, 2025

(54) ACRIDINIUM ESTER-CONTAINING COMPOUNDS AND METHODS OF USING THE SAME FOR CHEMILUMINESCENCE-BASED ONE-COLOR SEQUENCING

(71) Applicant: MGI Holdings Co., Limited, Guangdong (CN)

(72) Inventors: Yan Chen, Sunnyvale, CA (US); Handong Li, San Jose, CA (US)

(73) Assignee: MGI Holdings Co., Limited, Shenzhen (CN)

( * ) Notice: Subject to any disclaimer, the term of this patent is extended or adjusted under 35 U.S.C. 154(b) by 453 days.

(21) Appl. No.: 16/987,092

(22) Filed: Aug. 6, 2020

(65) Prior Publication Data

US 2021/0040556 A1    Feb. 11, 2021

Related U.S. Application Data

(60) Provisional application No. 62/883,760, filed on Aug. 7, 2019.

(51) Int. Cl.
*C12Q 1/6874* (2018.01)
*C07D 401/12* (2006.01)
*G01N 21/76* (2006.01)

(52) U.S. Cl.
CPC ......... *C12Q 1/6874* (2013.01); *C07D 401/12* (2013.01); *G01N 21/76* (2013.01)

(58) Field of Classification Search
CPC ..... C12Q 1/6874; C07D 401/12; G01N 21/76
See application file for complete search history.

(56) References Cited

U.S. PATENT DOCUMENTS

| 6,018,047 | A  | * | 1/2000  | Zomer ............... C09K 11/07 546/102 |
| 9,222,132 | B2 |   | 12/2015 | Drmanac |
| 2005/0147965 | A1 |  | 7/2005 | Zhong et al. |
| 2007/0166759 | A1 | * | 7/2007 | Weeks ............... C04B 35/632 435/7.1 |
| 2009/0263802 | A1 |  | 10/2009 | Drmanac |
| 2018/0223358 | A1 |  | 8/2018 | Drmanac et al. |
| 2018/0346980 | A1 |  | 12/2018 | Drmanac |

FOREIGN PATENT DOCUMENTS

| EP | 0324202 A1 | 7/1989 |
| EP | 0609885 A1 | 8/1994 |
| JP | 2012020958 A | 2/2012 |

(Continued)

OTHER PUBLICATIONS

Guo et al. (Account of Chemical Research, vol. 43, No. 4, Apr. 2010, p. 551-563) (Year: 2010).*

(Continued)

*Primary Examiner* — James H Alstrum-Acevedo
*Assistant Examiner* — Chantal Adlam
(74) *Attorney, Agent, or Firm* — Kilpatrick Townsend & Stockton LLP

(57) ABSTRACT

Acridinium ester-containing compounds are provided herein. Also provided herein are chemiluminescence-based one-color sequencing methods and methods of using the acridinium ester-containing compounds in chemiluminescence-based one-color sequencing.

9 Claims, 1 Drawing Sheet

Surfactant Effect on Different AE Structure

Two Acridinium Ester Structure Reaction Kinetics under Different Conditions

(56) References Cited

FOREIGN PATENT DOCUMENTS

| WO | 0109372 A1 | 2/2001 |
| WO | 2004018418 A2 | 3/2004 |
| WO | 2005065350 A2 | 7/2005 |
| WO | 2009097368 A2 | 8/2009 |
| WO | 2018165207 A1 | 9/2018 |

OTHER PUBLICATIONS

Natrajan et al., Org. Biomol. Chem., 2013, 11, 1026-1039. DOI: https://doi.org/10.1039/C2OB27190G (Year: 2013).*

International Application No. PCT/CN2020/107298, International Preliminary Report on Patentability mailed on Feb. 17, 2022, 6 pages.

Blackburn et al., "Management of Incidental Findings in the Era of Next-generation Sequencing", Curr. Genomics, 2015, pp. 159-174, vol. 16, No. 3.

Stranneheim et al., "Stepping stones in DNA sequencing", Biotechnol. J., Aug. 8, 2012, pp. 1063-1073, vol. 7, Issue 9.

Guo et al., "An Integrated System for DNA Sequencing by Synthesis Using Novel Nucleotide Analogues", Acc. Chem. Res., Feb. 3, 2010, pp. 551-563, 43, 4.

Mardis, "Next-Generation Sequencing Platforms", Annu. Rev. Anal. Chem., Jun. 2013, pp. 287-303, vol. 6.

Metzker, "Sequencing technologies—the next generation", Nat. Rev. Genet., Dec. 8, 2009, pp. 31-46, 11.

Goodwin et al., "Coming of age: ten years of next-generation sequencing technologies", Nat. Rev. Genet., May 17, 2016, pp. 333-351, 17.

Application PCT/CN2020/107298, International Search Report and Written Opinion, Nov. 10, 2020, 9 pages.

Application No. CN202080056098.6 , Office Action, Mailed on Apr. 4, 2023, 8 pages, Translation begins on p. 7.

European Application No. EP20849079.7, Partial Supplementary European Search Report mailed on Sep. 29, 2023, 14 pages.

Holec-Gasior et al., A Novel Chemiluminescent Immunoassay for Detection of Toxoplasma Gondii IgG in Human Sera, Diagnostic Microbiology and Infectious, vol. 85, No. 4, May 2016, pp. 422-425.

European Application No. 20849079.7, Extended European Search Report mailed on Jan. 10, 2024, 12 pages.

* cited by examiner

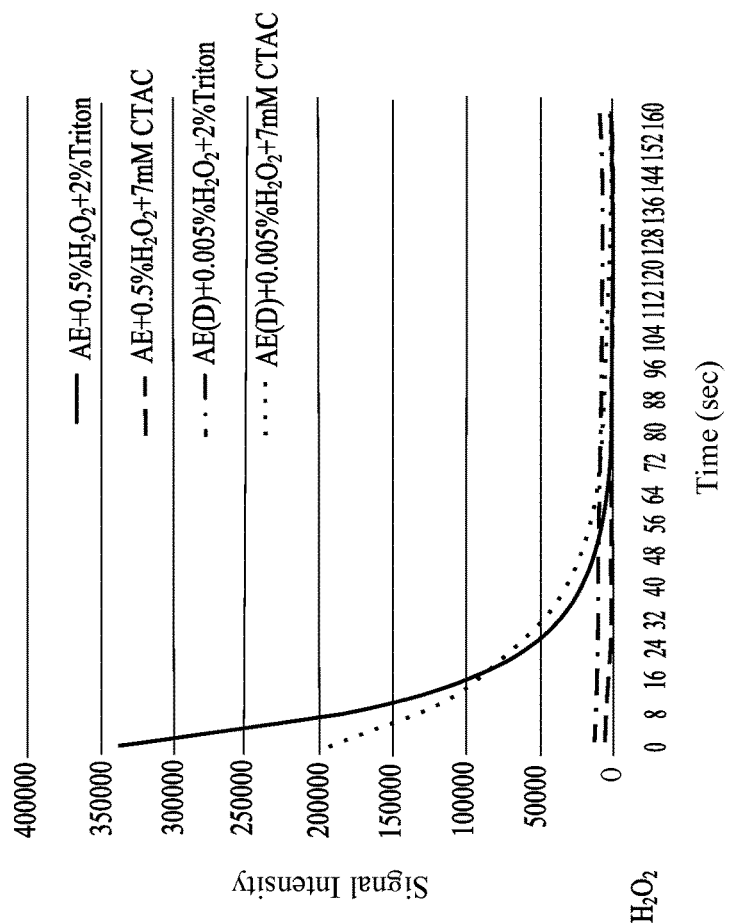
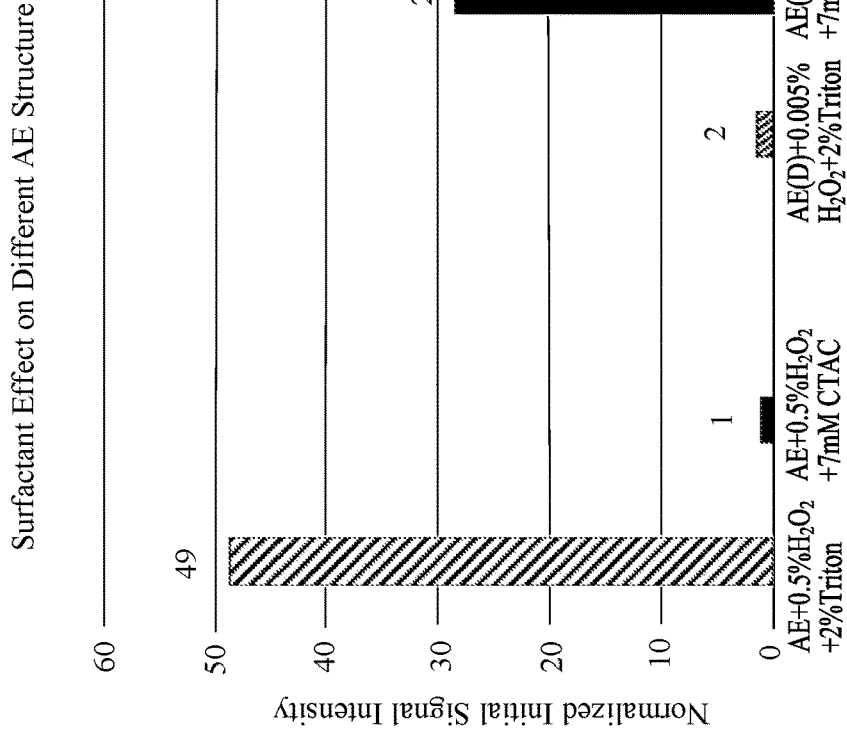

ACRIDINIUM ESTER-CONTAINING COMPOUNDS AND METHODS OF USING THE SAME FOR CHEMILUMINESCENCE-BASED ONE-COLOR SEQUENCING

CROSS-REFERENCE TO RELATED APPLICATION

This application claims priority to U.S. Provisional Patent Application No. 62/883,760, filed Aug. 7, 2019. This application is incorporated herein by reference in its entirety for all purposes.

FIELD

Disclosed herein are acridinium ester-containing compounds, and methods of using the acridinium ester-containing compounds in chemiluminescence-based one-color nucleic acid sequencing.

BACKGROUND

Chemiluminescence refers to a chemical reaction resulting in the production of light. When applied to a sequencing platform, chemiluminescence has limited value due to the structure design of currently available chemiluminescence molecules. Currently available chemiluminescence molecules, such as luminol, hydrogen peroxide, fluorescein, dioxetanes, and oxalate derivatives, suffer from signal diffusion due to the signaling molecule being separated from the tri-phosphate reversible terminator after excitation. Therefore, chemiluminescence is not typically used in sequencing methods, which require signal localization.

SUMMARY

Described herein are novel acridinium-ester-containing compounds (AE compounds) of the following formula:

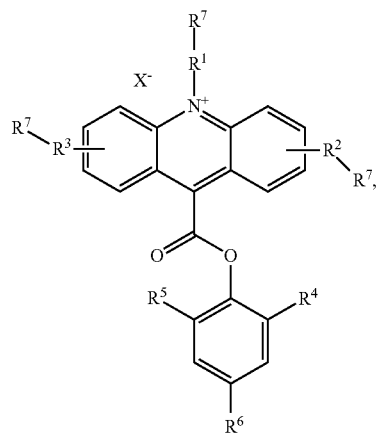

wherein $R^1$, $R^2$, and $R^3$ are each independently absent or a linking group. In some embodiments, the linking group is selected from the group consisting of substituted or unsubstituted alkoxy, substituted or unsubstituted alkyl, substituted or unsubstituted alkenyl, substituted or unsubstituted alkynyl, and substituted or unsubstituted aryl. $R^4$, $R^5$, and $R^6$ are each independently selected from the group consisting of hydrogen, substituted or unsubstituted $C_{1-8}$ alkyl, substituted or unsubstituted $C_{2-8}$ alkenyl, and substituted or unsubstituted $C_{2-8}$ alkynyl. Each $R^7$ is independently absent, hydrogen, a protein (e.g., an antibody) or a nucleotide moiety of the following formula:

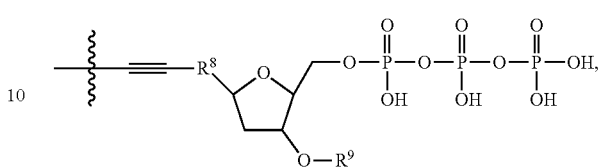

wherein $R^8$ is a nitrogenous base and $R^9$ is hydrogen or a blocking group; and $X^-$ is a counteranion. In the compound, only one $R^7$ present in the compound is a nucleotide moiety.

Optionally, $R^4$, $R^5$, and $R^6$ are not substituted with the nucleotide moiety. In some cases, $R^4$, $R^5$, and $R^6$ are each independently selected from the group consisting of hydrogen and substituted or unsubstituted $C_{1-6}$ alkyl. In some cases, $R^4$, $R^5$, and $R^6$ are each independently selected from hydrogen and methyl. Optionally, $R^4$ is methyl, $R^5$ is methyl, and $R^6$ is hydrogen. Optionally, each of $R^4$, $R^5$, and $R^6$ is hydrogen.

In some cases, $R^7$ is a nucleotide moiety as shown above. In these cases, $R^8$ can be a nitrogenous base selected from the group consisting of:

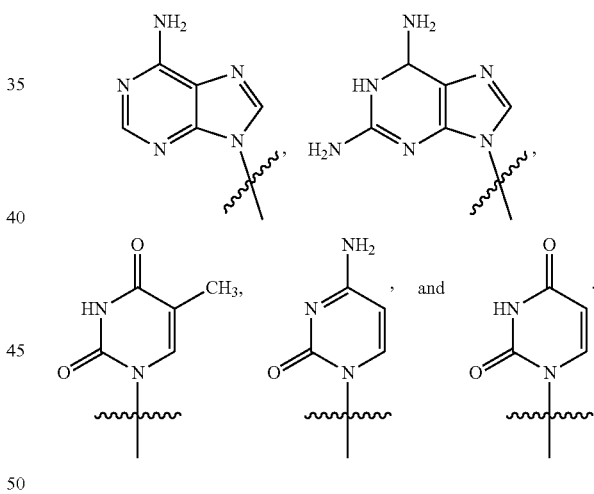

Optionally, $R^9$ can be a blocking group, wherein the blocking group is selected from the group consisting of —$CH_2N_3$, —$NH_2$, —$CH_2CH=CH_2$, —$CH_2OCH_3$, polyethylene glycol, and a substituted or unsubstituted alkyl. Optionally $R^9$ may be a blocking group selected from the group consisting of:

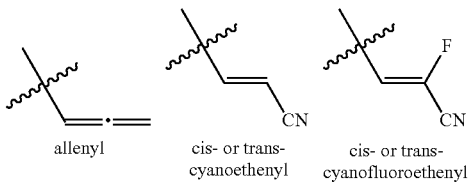

allenyl · cis- or trans-cyanoethenyl · cis- or trans-cyanofluoroethenyl

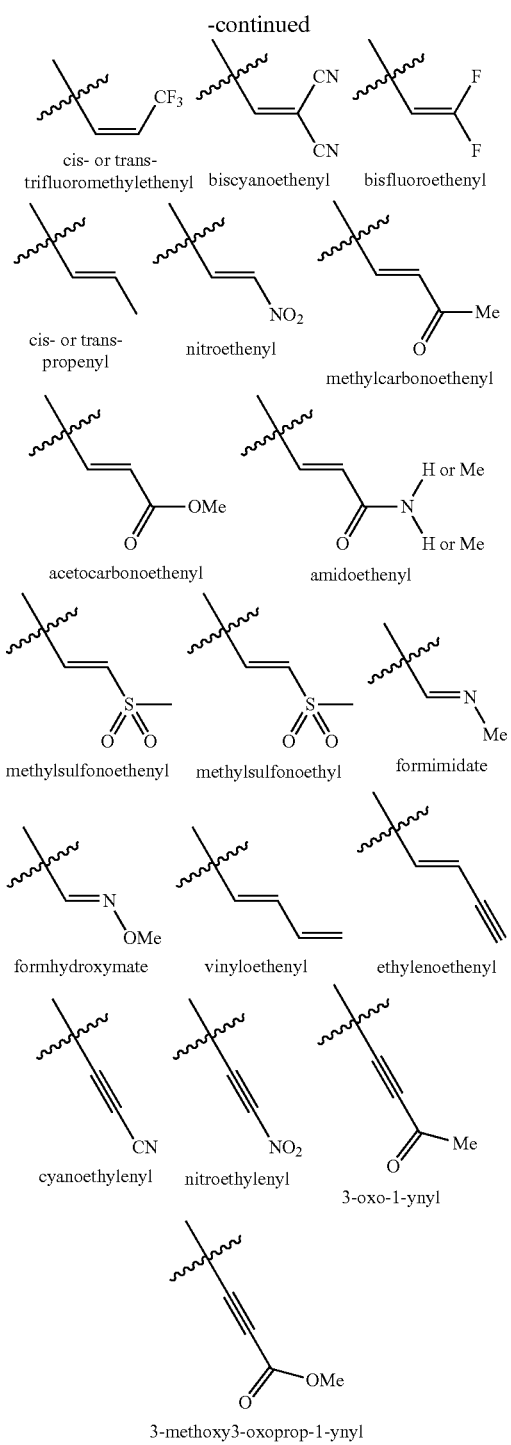

Also described herein are compositions comprising a mixture of deoxyribonucleotide triphosphates (dNTPs), the composition comprising: (i) first dNTPs conjugated to a first member of an AE pair; (ii) second dNTPs conjugated to a second member of the AE pair; (iii) third dNTPs conjugated to both the first member and the second member; and (iv) fourth dNTPs conjugated to neither the first member or the second member, wherein each of the first, second, third, and fourth dNTPs is selected from the group consisting of dATP, dTTP, dCTP, and dGTP, and are different from each other; and wherein the first member and second member have distinguishable properties. In some embodiments, the first member and the second member have minimal cross talk. Optionally, the dNTPs are reversible terminator dNTPs comprising cleavable blocking groups.

Further described herein are methods for identifying bases of a plurality of template DNA strands having different sequences. The methods can comprise i) providing an array of immobilized template DNA strands annealed to a primer or primer extension product; ii) contacting the array of (i) with the composition described above in the presence of a DNA polymerase under conditions in which the primers or primer extension products are extended by incorporation of a dNTP; iii) contacting the array with a first solution and capturing a first image; iv) contacting the array with a second solution and capturing a second image; and v) comparing the first and second images to identify bases of the plurality of template DNA strands.

The details of one or more embodiments are set forth in the drawings and the description below. Other features, objects, and advantages will be apparent from the description and drawings, and from the claims.

BRIEF DESCRIPTION OF THE DRAWINGS

FIG. 1 shows surfactant affects initial signal intensity for two AE compounds. In FIG. 1, "AE" means "AE-H" and "AE(D)" means "AE-D".

DETAILED DESCRIPTION

I. Definitions

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. Likewise, the term aryloxy as used herein is an aryl group bound through a single, terminal ether linkage.

The terms amine or amino as used herein are represented by the formula —$NZ^1Z^2$, where $Z^1$ and $Z^2$ can each be a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, and aryl molecules used herein can be substituted or unsubstituted. As used herein, the term substituted includes the addition of a substitution group to a position attached to the main chain of the alkoxy, aryloxy, amino, alkyl, alkenyl, alkynyl, and aryl, e.g., the replacement of a hydrogen by a substitution group. Examples of substitution groups include, but are not limited to, hydroxyl, halogen (e.g., F, Br, Cl, or I), and carboxyl groups. Conversely, as used herein, the term unsubstituted indicates the alkoxy, aryloxy, amino, alkyl, alkenyl, alkynyl, or aryl has a full complement of hydrogens, i.e., commensurate with its saturation level, with no substitutions, e.g., linear decane (—$(CH_2)_9$—$CH_3$).

II. Compositions

Described herein are acridinium-ester containing compounds including a nucleotide moiety. As used herein, the term "nucleotide moiety" refers to a group that includes a nitrogenous base, a sugar component (e.g., a 5-carbon sugar) or a derivative thereof, and at least one phosphate group.

The acridinium-ester containing compounds described herein include compounds represented by Formula I:

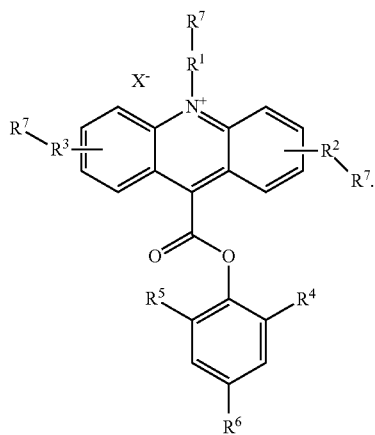

In Formula I, $R^1$, $R^2$, and $R^3$ are each independently absent or a linking group. As used herein, "linking group" refers to a moiety positioned between a location on the acridinium moiety and the $R^7$ group, which is further defined below. In some embodiments, the linking group is selected from the group consisting of substituted or unsubstituted alkoxy, substituted or unsubstituted alkyl (e.g., $C_{1-8}$ substituted or unsubstituted alkyl), substituted or unsubstituted alkenyl (e.g., $C_{2-8}$ substituted or unsubstituted alkenyl), substituted or unsubstituted alkynyl (e.g., $C_{3-8}$ substituted or unsubstituted alkynyl), and substituted or unsubstituted aryl. Optionally, $R^1$, $R^2$, and/or $R^3$ is absent, meaning a linking group is not present as $R^1$, $R^2$, and/or $R^3$. In these embodiments, $R^7$ is attached directly to the acridinium moiety.

Also in Formula I, $R^4$, $R^5$, and $R^6$ are each independently selected from the group consisting of hydrogen, substituted or unsubstituted $C_{1-8}$ alkyl, substituted or unsubstituted $C_{2-8}$ alkenyl, and substituted or unsubstituted $C_{2-8}$ alkynyl. Optionally, $R^4$, $R^5$, and $R^6$ are not substituted with the nucleotide moiety. In some cases, $R^4$, $R^5$, and $R^6$ are each independently selected from the group consisting of hydrogen and substituted or unsubstituted $C_{1-6}$ alkyl. In some cases, $R^4$, $R^5$, and $R^6$ are each independently selected from hydrogen and methyl. In some embodiments, $R^4$ and $R^5$ are the same (e.g., both $R^4$ and $R^5$ are hydrogen or both $R^4$ and $R^5$ are substituted or unsubstituted $C_{1-8}$ alkyl, such as methyl). Optionally, $R^4$ is methyl, $R^5$ is methyl, and $R^6$ is hydrogen. Optionally, each of $R^4$, $R^5$, and $R^6$ is hydrogen.

Additionally in Formula I, each $R^7$ is independently absent, hydrogen, a protein (e.g., an antibody), or a nucleotide moiety represented by Structure A:

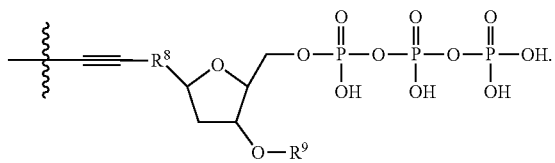

In Structure A, $R^8$ is a nitrogenous base, as further defined below, and $R^9$ is hydrogen or a blocking group, as further defined below.

In some cases, only one of the three $R^7$ groups present in the compounds according to Formula I is a nucleotide moiety represented by Structure A. For example, if the $R^7$ group linked to $R^1$ is a nucleotide moiety, then the $R^7$ groups linked to $R^2$ and $R^3$ are independently absent or hydrogen. Similarly, if the $R^7$ group linked to $R^2$ is a nucleotide moiety, then the $R^7$ groups linked to $R^1$ and $R^3$ are independently absent or hydrogen. Likewise, if the $R^7$ group linked to $R^3$ is a nucleotide moiety, then the $R^7$ groups linked to $R^1$ and $R^2$ are independently absent or hydrogen.

In some cases, $R^7$ is a nucleotide moiety. In these cases, $R^8$ can be a nitrogenous base. Exemplary nitrogenous bases include adenine (A), cytosine (C), guanine (G), thymine (T), uracil (U), inosine (I), and derivatives of these. Exemplary nitrogenous bases are shown below:

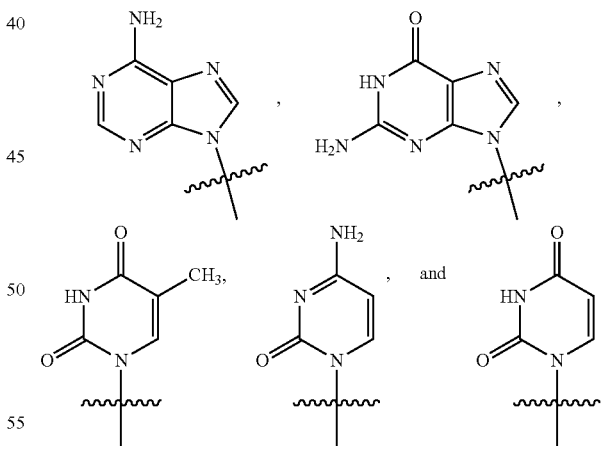

In one aspect, the nitrogenous base is a 7-deaza derivative of adenine, inosine, or guanine. In some cases, the 7-deaza adenine, inosine, and/or guanine derivatives are linked to the alkyne group in $R^7$ through the 7-position (i.e., the 7-deaza adenine, inosine, and/or guanine derivatives are 7-substituted with $R^7$ through $R^7$'s alkyne group). In some cases, uracil, cytosine, thymine, and/or derivatives thereof are 5-substituted. For example, the 5-substituted uracil, cytosine, thymine, and/or derivatives thereof can be attached to the alkyne group in $R^7$ through the 5-position (i.e., the 5-substituted uracil, cytosine, thymine, and/or derivatives thereof are substituted with $R^7$ through $R^7$'s alkyne group).

Optionally, $R^9$ can be hydrogen or a blocking group. As used herein, the term "blocking group" refers to any group that can be cleaved to provide a hydroxyl group at the 3'-position of the nucleotide analogue. The blocking group can be cleavable by physical means, chemical means, heat, and/or light. Optionally, the blocking group is cleavable by enzymatic means. In some embodiments, the blocking group is an azido-containing blocking group (e.g., —$CH_2N_3$). In some embodiments, the blocking group is an amino-containing blocking group (e.g., —$NH_2$). In some embodiments, the blocking group is an allyl-containing blocking group (e.g., —$CH_2CH=CH_2$). In some embodiments, the blocking group is an alkoxy-containing blocking group (e.g., —$CH_2OCH_3$) or an aryloxy-containing blocking group (e.g., —$CH_2OPh$). In some embodiments, the blocking group is polyethylene glycol (PEG). In some embodiments, the blocking group is a substituted or unsubstituted alkyl (i.e., a substituted or unsubstituted hydrocarbon). Optionally, $R^9$ can be a group as shown below:

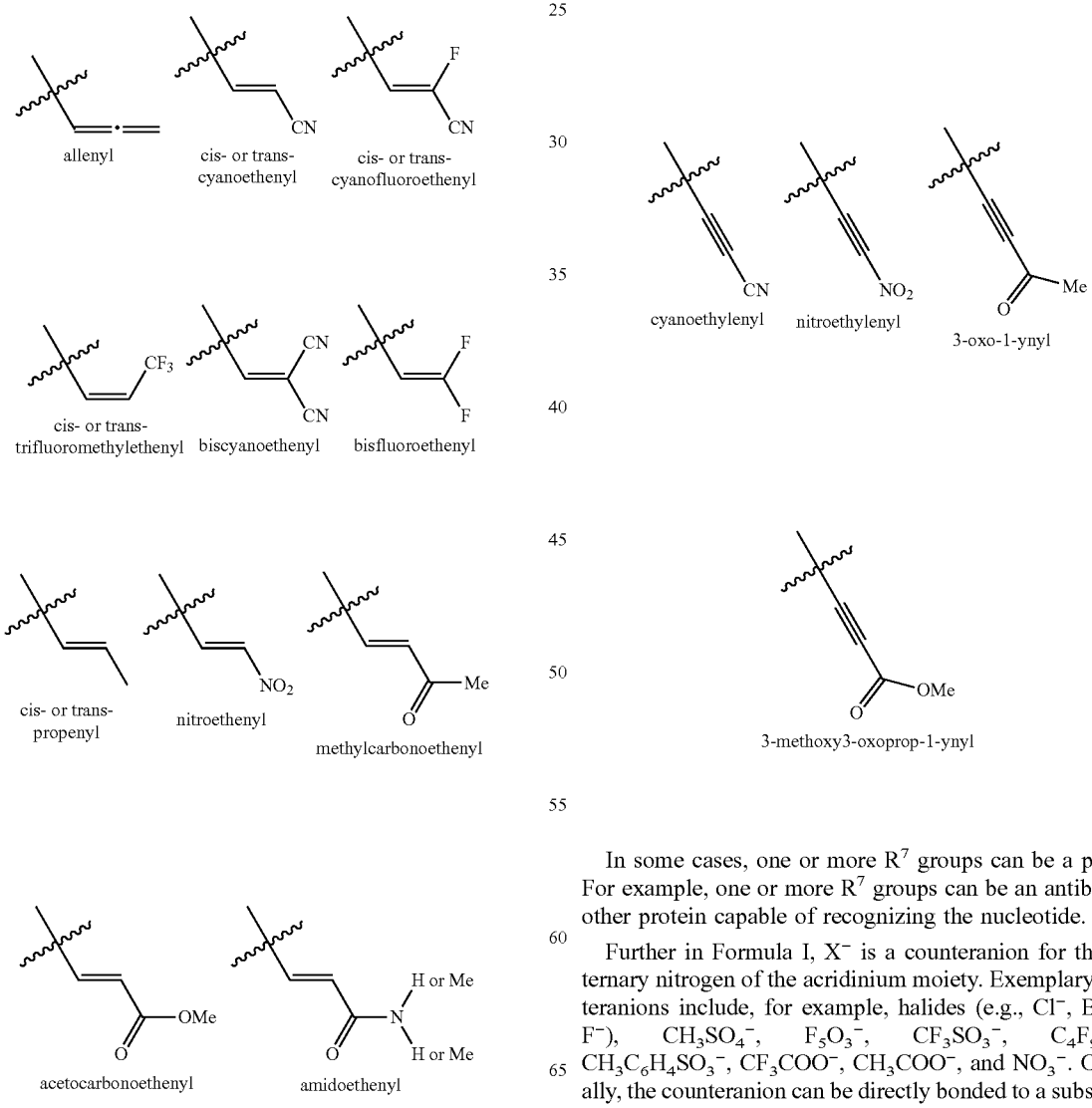

In some cases, one or more $R^7$ groups can be a protein. For example, one or more $R^7$ groups can be an antibody or other protein capable of recognizing the nucleotide.

Further in Formula I, $X^-$ is a counteranion for the quaternary nitrogen of the acridinium moiety. Exemplary counteranions include, for example, halides (e.g., $Cl^-$, $Br^-$, $I^-$, $F^-$), $CH_3SO_4^-$, $F_5O_3^-$, $CF_3SO_3^-$, $C_4F_9SO_3^-$, $CH_3C_6H_4SO_3^-$, $CF_3COO^-$, $CH_3COO^-$, and $NO_3^-$. Optionally, the counteranion can be directly bonded to a substituent in Formula I.

Examples of acridinium-ester containing compounds according to Formula I include the following:

Formula I-A

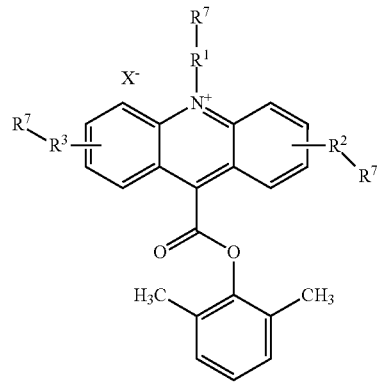

Formula I-B

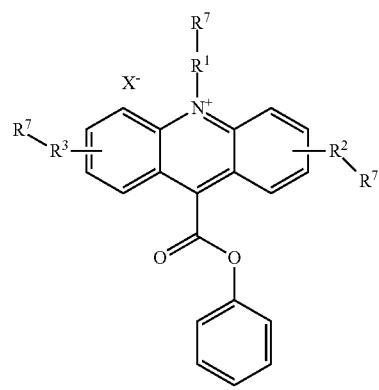

In Formula I-A and Formula I-B, X R$^1$, R$^2$, R$^3$, and each R$^7$ are as defined above for Formula I. Formula I-A may be referred to as "AE-D" (AE-dimethyl) and Formula I-B may be referred to as "AE-H" (AE-hydrogen).

In some examples, the compounds according to Formula I-B are represented by one of the following:

Compound 1A

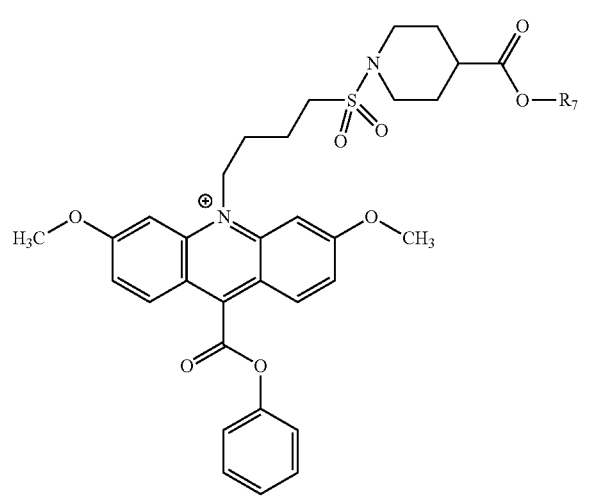

Compound 1B

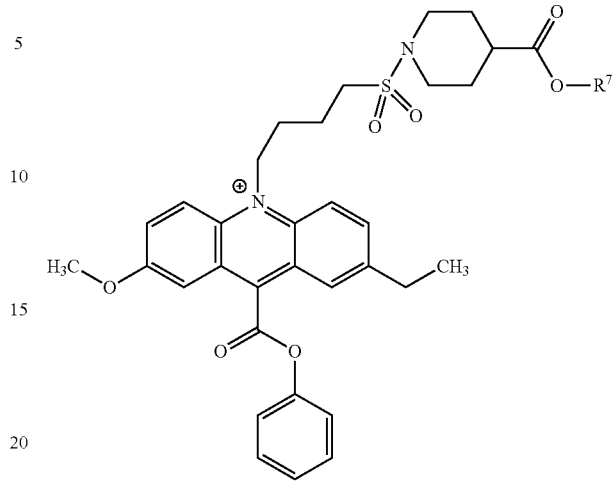

In some examples, the compounds according to Formula I-A are represented by one of the following:

Compound 2A

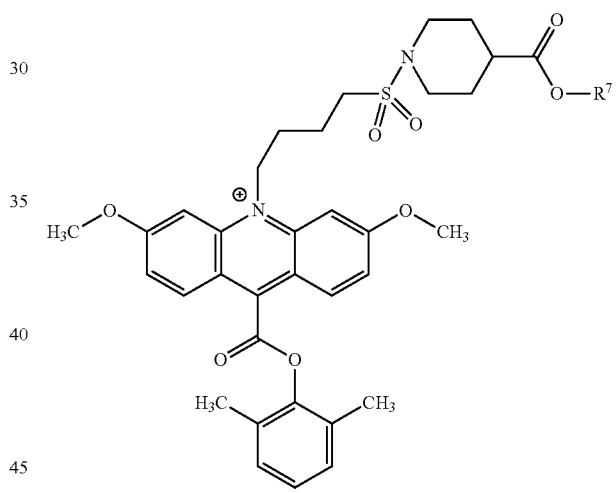

Compound 2B

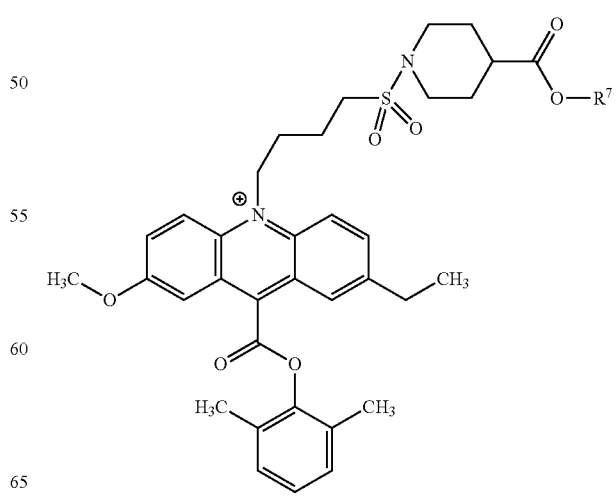

The compounds described herein can be prepared in a variety of ways known in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I and the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety. The synthesis and subsequent testing of various compounds as described herein to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry (MS), or by chromatography such as high performance liquid chromatography (HPLC) or thin layer chromatography (TLC).

Optionally, the compounds described herein can be synthesized by using commercially available dNTPs. The commercially available dTNPs can be conjugated to a linker or a binding molecule through a phosphate conjugation reaction. The 3'-position of the dNTPs can be blocked by reacting the compounds with a protecting group. The conjugating and blocking reactions can be performed in any order.

Signal localization achieved by the acridinium ester-triphosphate reversible terminator conjugates as described herein is depicted through the reaction mechanism shown below in Scheme 1.

Scheme 1: Signal Localization Reaction Mechanism

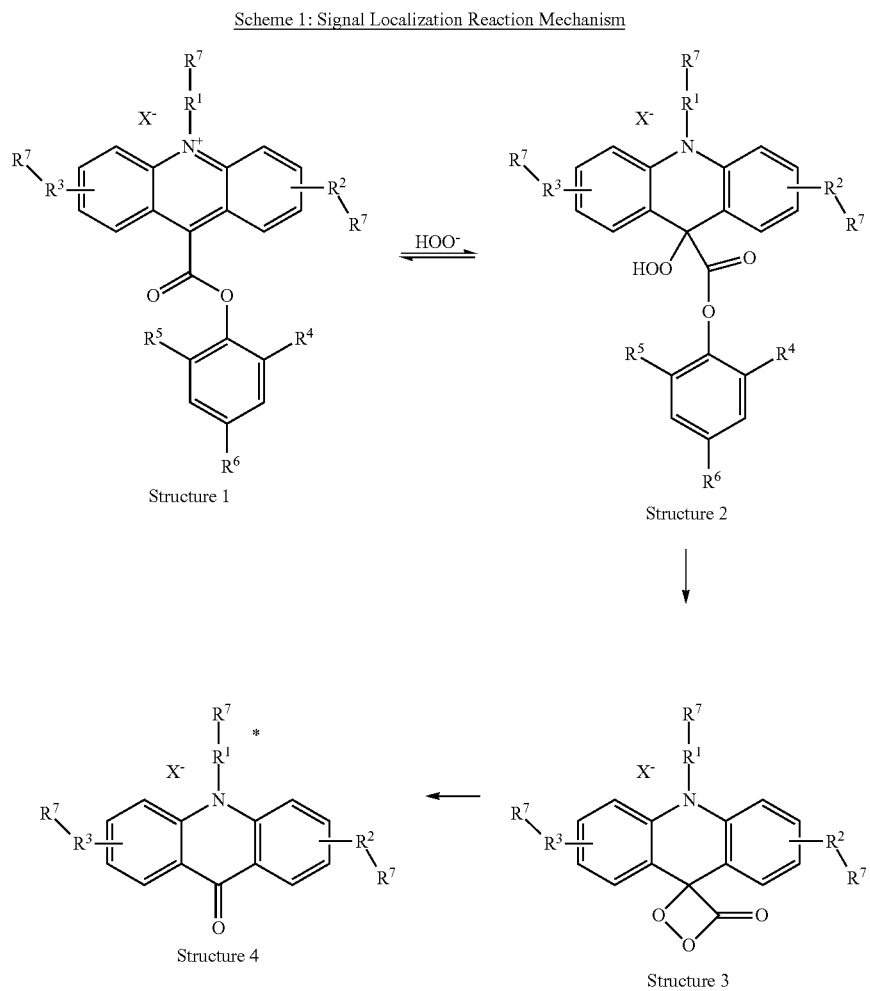

As shown above in Scheme 1, an acridinium ester compound as described herein (Structure 1) is exposed to a peroxide source. The hydrogen peroxide anion then attacks the acridinium moiety to form Structure 2, which triggers an intramolecular nucleophilic attack on the carbonyl group to form the dioxetane intermediate Structure 3. Structure 3 is highly strained and decomposes to form Structure 4 and emit light. Structure 4, which is the acridinium moiety after excitation (as indicated by the asterisk), remains linked to the tri-phosphate reversible terminator (i.e., $R^7$).

III. AE Pairs with Distinguishable Properties or Minimal Cross Talk

Advantageously, AE pairs with different signal producing properties find use in nucleic acid sequencing methods, such as sequencing-by-synthesis (SBS) methods. In one approach, the AE pair comprises a first compound of Formula I-A (AE-D) and a second compound of Formula I-B (AE-H), such as Compound 2B and Compound 1B or Compound 2A and Compound 1A. Suitable AE pairs can be determined using methods known to those of ordinary skill in the art.

Different signal producing properties of AEs include light emission at different initial signal intensities when in the presence of peroxide (e.g., hydrogen peroxide or a hydrogen peroxide-urea complex) and surfactants (e.g., Triton X-100 (4-(1,1,3,3-tetramethylbutyl)phenyl-polyethylene glycol) or Triton X-114 ((1,1,3,3-tetramethylbutyl)phenyl-polyethylene glycol)). For example, AE-H and AE-D may emit light at high or very low (e.g., zero) initial signal intensities depending on peroxide concentration and the presence, absence, or level of certain surfactants. For illustration, Table 1 shows exemplary conditions in which an AE pair (AE-D and AE-H) emit light at different intensities. Desirably, and as shown in Table 1 and FIG. 1, the two AE members of an AE pair have minimal cross-talk under a predetermined conditions.

In one approach, the predetermined conditions comprise a peroxide concentration and a surfactant type and concentration.

In one approach, "minimal cross talk" means that under a first predetermined condition the initial signal intensity from a first member of an AE pair is at least 10, at least 50, at least 100, at least 500, or at least 1000-fold greater than the initial signal intensity of a second member of the AE pair under the first predetermined condition, and that under a second predetermined condition the initial signal intensity from the second first member of the AE pair is at least 10, at least 50, at least 100, at least 500, or at least 1000-fold greater than the initial signal intensity of the first member of the AE pair under the second predetermined condition. In one embodiment, "minimal cross talk" means that under a first predetermined condition the initial signal intensity from a first member of an AE pair is at least 50-fold greater than the initial signal intensity of a second member of the AE pair under the first predetermined condition, and that under a second predetermined condition the initial signal intensity from the second first member of the AE pair is at least 50-fold greater than the initial signal intensity of the first member of the AE pair under the second predetermined condition.

Table 1 and FIG. 1 illustrate conditions under which the AE pair comprising AE-D (identified as "AE(D)" in FIG. 1) and AE-H (identified as "AE" in FIG. 1) have minimal cross-talk. The AE pair used in this illustration are Compound 2B and Compound 1B.

TABLE 1

| | $[H_2O_2]$ | Surfactant |
|---|---|---|
| AE-D emits strong signal, AE-H does not emit signal | Low $H_2O_2$ concentration (0.005%) | CTAT (7 mM) |
| AE-H emits strong signal, AE-D does not emit signal | High $H_2O_2$ concentration (0.5%) | Triton X-100 (2%) |

As noted, first and second predetermined conditions may include peroxide concentration and surfactant type and concentration. Exemplary peroxide concentrations may range from, for example and not limitation, 0.0005% to 0.010% (e.g., 0.005%), sometimes referred to as "low concentration," and from 0.011% to 1.0% (e.g., 0.5%), sometimes referred to as "high concentration."

Exemplary surfactants include cationic, anionic, and non-ionic surfactants. In some examples, the surfactants can include Triton X-100 (4-(1,1,3,3-tetramethylbutyl)phenyl-polyethylene glycol), cetyltrimethylammonium tosylate (CTAT), other surfactants shown in Table 2, and combinations of surfactants. Optimal concentrations of each surfactant for use with a given AE pair may be determined empirically. Useful concentrations of CTAT include the range 1.0 mM to 10.0 mM (e.g., 7 mM), and useful concentrations for Triton X-100 include 0.5% to 5% (e.g., 2%). Other exemplary concentrations for surfactants are shown in Table 2.

TABLE 2

| Surfactant | Abbreviation | Exemplary Concentration |
|---|---|---|
| Cetyltrimethylammonium Chloride | CTAC | 7.8 mM |
| Dihexadecyldimethylammonium Bromide | DHDAB | 10 mM |
| Didodecyldimethylammonium Bromide | DDDAB | 10 mM |
| Trimethyloctadecylammonium Chloride | TMDAC | 10 mM |
| Dimethyldioctadecylammonium Bromide | DMDAB | 1 mM |
| Tetrahexylammonium Chloride | THAC | 10 mM |
| Tridodecylmethylammonium Chloride | TDMAC | 1 mM |
| Tetradodecylammonium Chloride | TDAC | 1 mM |

IV. One Color Sequencing

Acridinium ester-tri-phosphate reversible terminator conjugates (AE pairs) may be used in nucleic acid sequencing methods. In some approaches, the sequencing method is massively parallel sequencing-by-synthesis (SBS). Methods for nucleic acid sequencing-by-synthesis (SBS) and other next generation sequencing (NGS) methods are well known. See Blackburn et al., Curr. Genomics 16(3):159-174 (2015); Stranneheim and Lundeberg, Biotechnol. J. 7:1063-73 (2012); Guo et al., Acc. Chem. Res. 43:551-563 (2010), Drmanac et al US20180223358A1; Mardis, E. R., 2013, Annu. Rev. Anal. Chem. 6:287-303; Metzker, M. L., 2010, Nat. Rev. Genet. 11:31-46; Goodwin et al., 2016, Nat. Rev. Genet. 17:333-351, each of which is incorporated herein by reference. In some cases, SBS methods use 3' blocked dNTPs with reversible terminator dyes, including but not limited to dyes as described in US Published Patent Application No. 2010/00317531 (incorporated herein by reference). In some cases, SBS methods are carried out using an ordered or patterned array in a flow-cell. Acridinium ester-tri-phosphate reversible terminator conjugates (AE pairs) disclosed herein find particular use in one-color (also called one-channel) sequencing. SBS may be carried out using clonal populations of template sequences prepared by bridge PCR, emulsion PCR, production of concatemers (DNA nanoballs) and other methods.

As used herein, "one-color sequencing" refers to massively parallel sequencing methods in which four bases can be distinguished based on differential emission of light under two different conditions. In one approach, the two conditions are exposure to two chemical environments. In one approach, the first condition and second condition are not different based on disassociation (e.g., by cleavage) or association (e.g., through a ligand antiligand interaction) of labels with nucleotides incorporated into a primer extension product or growing strand such as produced in a nucleic acid sequencing method. The light emitted under the two conditions may be the same wavelength, different wavelengths, or approximately the same wavelength, e.g., differing less than 500 nm, 200 nm or 100 nM. See U.S. Pat. No. 9,222,132, incorporated herein by reference, for a non-limiting description of certain one-color methods. Using one-color sequencing methods, different bases (e.g., A, T, C, G) are distinguished based on detection of signal at different intensity (or 'brightness'), including zero intensity (no signal), under different conditions (e.g., under a first predetermined condition and a second predetermined condition).

The sequencing methods described herein make use of acridinium ester-tri-phosphate reversible terminator conjugates described herein. Generally, a mixture of four nucleotide analogs (dATP, dTTP, dCTP, dGTP) is used. For example, in one approach one dNTP analog is labeled with (conjugated to) AE-D, a second dNTP analog is labeled with AE-H, a third dNTP analog is dual labeled with AE-D and AE-H, and a fourth dNTP is not labeled with an AE. The dual-labeled dNTP may be labeled in a variety of ways. In one approach, some or all of the dual-labeled dNTP molecules (e.g., dTTP) are physically labeled with two different labels (AE-D and AE-H). In another approach, a mixture of the double labeled dNTP molecules (e.g., dTTP) is used in which some dNTPs are labeled with AE-D and some are labeled with AE-H. In one approach, the mixture includes about equimolar amounts of AE-D labeled and AE-H labeled molecules.

In one approach, the reversible terminator conjugates described herein are used in sequencing-by-synthesis (SBS) methods. It will be understood by those of skill in the art that generally reversible terminator dNTPs comprise blocking groups that are removed ("deblocking") at the end of each sequencing cycle to regenerate a 3'-OH on the deoxyribose sugar and permit incorporation of the nucleotide complementary to the template nucleotide at the next sequencing position.

In one common SBS approach, one nucleotide is incorporated in each sequencing cycle. Typically, in each sequencing cycle, a reversible terminator dNTP is incorporated into a growing strand, the incorporation is detected, and the terminator is removed ("deblocking"). According to the present invention, the incorporated dNTP is exposed to two predetermined conditions in each cycle (or one predetermined condition in each half-cycle). In one approach, an array of clonal clusters (e.g., produced by bridge PCR), single molecules, DNA nanoballs, or the like, is produced in a sequencing flow cell, comprising (1) a substrate on which target molecules (e.g., target amplicons) are immobilized and (2) a fluidic system that allows reagents, enzymes, buffers, washes, and the like to be delivered to the substrate. In one approach, it is a patterned flow cell. After each dNTP incorporation step, a first solution is flowed through the flow cell (e.g., low $H_2O_2$ plus CTAT) and an image is collected, and then a second solution is flowed through the flow cell (e.g., high $H_2O_2$ plus Triton) and a second image is collected. The pair of images is compared and the identity of the incorporated dNTP is determined as discussed below and described in Tables 3 and 4.

As used herein, an "image" or "imaging" refers to collection of data (light emission intensity) and is not limited to a particular system or format of collection. For example, "images" may be collected using CCD cameras, complementary metal-oxide semiconductor (CMOS) chips, and other detectors. "Comparing" images generally comprises analysis of signal date using a computer.

Each flow step may be continuous or discontinuous and optionally buffer washes may be carried out before, between, or after exposure to each solution. The first and second images are compared and changes in signal emissions of one or more AE-rtNTPs are determined. By comparing the signals at each position on an array, the incorporated nucleotide may be identified.

TABLE 3

| dNTP analog | Signal captured in 1st image | Signal captured in 2nd image |
| --- | --- | --- |
| dNTP-1 (e.g., dATP conjugated to AE-D) | Absent or low | Present or high |
| dNTP-2 (e.g., dCTP) conjugated to AE-H | Present or high | Absent or low |
| dNTP-3 (e.g., dTTP) conjugated to AE-D and AE-H | Present or high | Present or high |
| dNTP-4 (e.g., dGTP) conjugated to neither AE-D or AE-H | Absent or low | Absent or low |

TABLE 4

| dNTP analog | Signal captured in 1$^{st}$ image | Signal captured in 2$^{nd}$ image |
| --- | --- | --- |
| dATP | 0 | 1 |
| dCTP | 1 | 0 |
| dTTP | 1 | 1 |
| dGTP | 0 | 0 |

EXAMPLES

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

Example 1: Synthesis of Acridinium Ester-Containing Compounds

General Procedure for the Preparation of Compound 3:

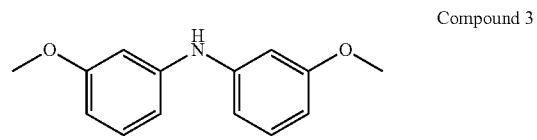

Compound 3

To a 250 mL flask, 3-bromoanisole (5.0 g), 3-methoxyaniline (4.0 g), palladium acetate (0.21 g), 2,2'-bis(diphenylphosphino)-1,1'-binaphthyl (BINAP; 0.8 g), cesium carbonate (9.6 g), and toluene (100 mL) were added. The mixture was degassed for 5 minutes and then refluxed for 3 days under Argon. Water was added to the cooled reaction mixture, followed by extraction with ethyl acetate (EtOAc). The extract was washed with water and dried over anhydrous sodium sulfate ($Na_2SO_4$). The crude product was purified by silica gel column chromatography to give Compound 3.

General Procedure for the Preparation of Compound 4:

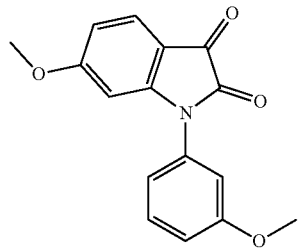

Compound 4

Compound 3 (2.5 g) in toluene (60 mL) was slowly added to a solution of oxalyl chloride (3.0 mL) in toluene (100 mL) using an additional funnel. After the addition was over, the mixture was heated at 60° C. for 1 hour. The solvent was removed and the residue was heated at 120° C. overnight. The resulting solid (Compound 4) was used in the reaction of the next step without purification.

General Procedure for the Preparation of Compound 5:

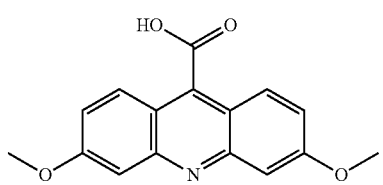

Compound 5

To the crude Compound 4 was added 2N NaOH/water (100 mL). The mixture was refluxed for 4 hours and then cooled to room temperature. An HCl/water mixture (2N) was added to adjust the pH to 1-3. The resulting yellow precipitate was collected and washed with water. The solid was dried to give Compound 5.

General Procedure for the Preparation of Compound 6:

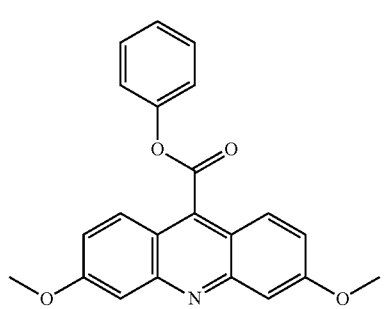

Compound 6

Compound 5 was suspended in thionyl chloride (12 mL) and two drops of dimethylformamide (DMF) was added. The mixture was refluxed for 2 hours, and then thionyl chloride was removed. Phenol (1.3 g), anhydrous dichloromethane ($CH_2Cl_2$; 20 mL), and pyridine (5 mL) were added to the residue. The mixture was refluxed for 2 hours, and then $CH_2Cl_2$ and pyridine were removed. The residue was dissolved in chloroform ($CHCl_3$) and washed with sodium bicarbonate ($NaHCO_3$)/water. The organic layer was dried over anhydrous $Na_2SO_4$. The crude product was purified by silica gel column chromatography to give Compound 6.

General Procedure for the Preparation of Compound 7:

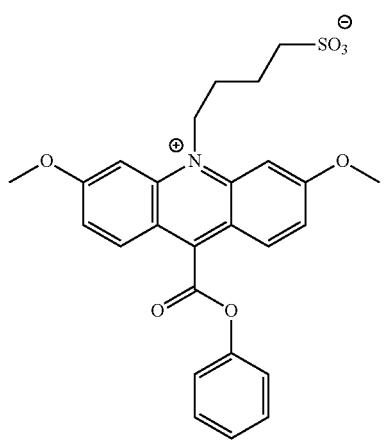

Compound 7

Compound 6 (0.5 g) and 1,4-butane sultone (10 g) were mixed and heated at 130° C. for 10 hours, and then cooled to room temperature. A solution of 1N HCl in water (100 mL) was added to the reaction mixture and the resulting mixture was heated at 60° C. for 30 minutes. The mixture was cooled to room temperature and then adjusted pH to 1-2 with $NaHCO_3$/water. The mixture was purified by $C^{18}$ column chromatography using 0.1% trifluoroacetic acid (TFA) buffer and acetonitrile ($CH_3CN$) as solvents to give Compound 7.

General Procedure for the Preparation of Compound 8:

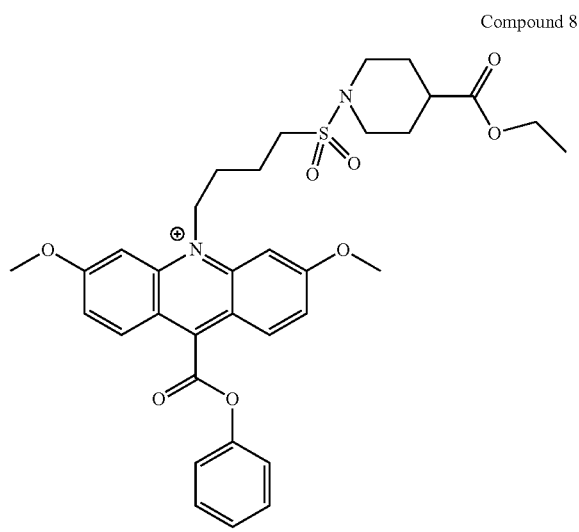 [SMILES: CCOC(=O)C1CCN(S(=O)(=O)CCCC[n+]2c3cc(OC)ccc3c(C(=O)Oc3ccccc3)c3ccc(OC)cc32)CC1]

Compound 8

Compound 7 (0.1 g) was suspended in anhydrous CH$_2$Cl$_2$ (5 mL). Oxalyl chloride (1 mL) was added to the mixture and the resulting mixture was stirred at room temperature for 2 hours. The solvent and oxalyl chloride were removed, the residue was dissolved in anhydrous CH$_2$Cl$_2$ (5 mL), and then ethyl isonipecotate (0.2 ml) was added. The mixture was stirred at room temperature for 10 minutes, and then 1N HCl/water was added. The mixture was extracted with CHCl$_3$, the solvent was removed to give Compound 8 without purification.

General Procedure for the Preparation of Compound 1:

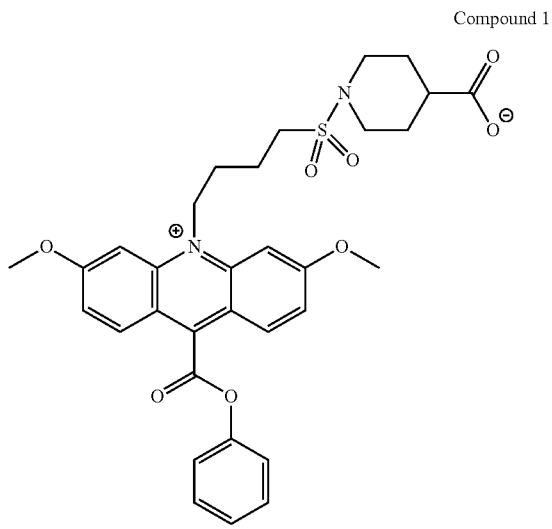 [SMILES: COc1ccc2c(C(=O)Oc3ccccc3)c3ccc(OC)cc3[n+](CCCCS(=O)(=O)N3CCC(C(=O)[O-])CC3)c2c1]

Compound 1

The above crude Compound 8 was suspended in dioxane (20 mL) and 1N HCl/water (40 mL), and the mixture was stirred at 70° C. for 4 hours. The dioxane was removed and the pH of the aqueous solution was adjusted to 1-2 with NaHCO$_3$/water. Acetonitrile was then added, resulting in a clear solution. The solution was purified by preparative HPLC using 0.1% TFA buffer and CH$_3$CN as solvents to give pure Compound 1.

General Procedure for the Preparation of Compound 2:
Compound 2 was synthesized using a similar procedure to that used to prepare Compound 1.

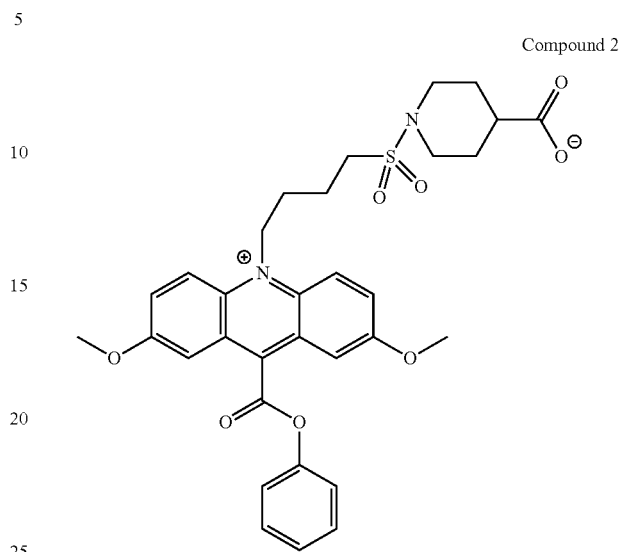

Compound 2

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound including a nucleotide moiety of the following formula:

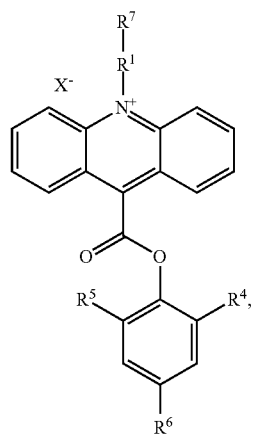

wherein:
R$^1$ is a linking group comprising a C$_1$-C$_8$ alkyl sulfonyl piperidine;
R$^4$, R$^5$, and R$^6$ are each independently selected from the group consisting of hydrogen, —CH$_3$, —OCH$_3$, substituted or unsubstituted C$_{1-8}$ alkyl, substituted or unsubstituted C$_{2-8}$ alkenyl, and substituted or unsubstituted C$_{2-8}$ alkynyl, wherein the substituted alkyl group or the substituted alkenyl group is independently substituted with one or more members selected from the group consisting of a hydroxyl, a halogen, and a carboxyl group;

R$^7$ is a nucleotide moiety of the following formula:

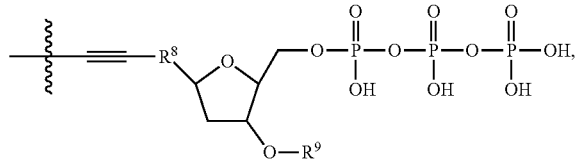

wherein

R$^8$ is the nitrogenous base, which is a member selected from the group consisting of:

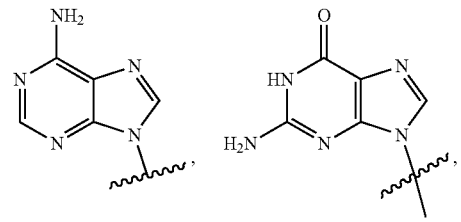

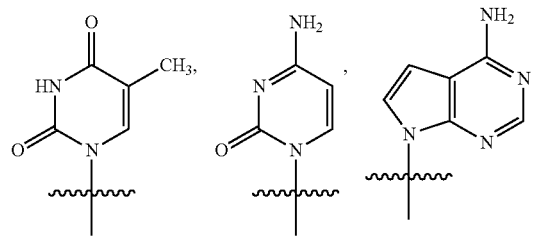

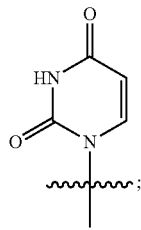

and

R$^9$ is hydrogen or a blocking group; and

X$^-$ is a counteranion.

2. The compound of claim 1, wherein R$^4$, R$^5$, and R$^6$ are each independently selected from the group consisting of hydrogen and substituted or unsubstituted C$_{1-6}$ alkyl.

3. The compound of claim 1, wherein R$^4$, R$^5$, and R$^6$ are each independently selected from hydrogen and methyl.

4. The compound of claim 1, wherein R$^4$ is methyl, R$^5$ is methyl, and R$^6$ is hydrogen.

5. The compound of claim 1, wherein each of R$^4$, R$^5$, and R$^6$ is hydrogen.

6. The compound of claim 1, wherein R$^7$ is the nucleotide moiety and R$^8$ is the nitrogenous base selected from the group consisting of:

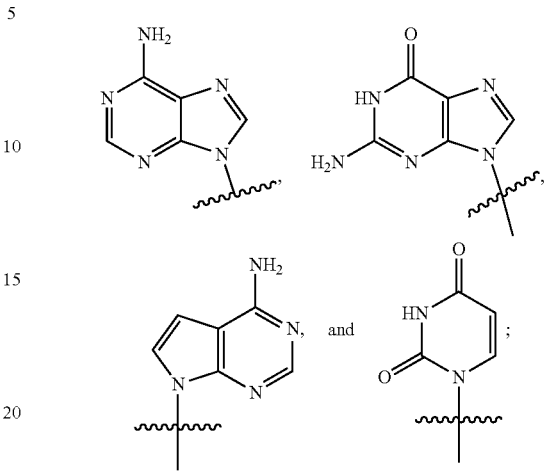

7. The compound of claim 1, wherein R$^9$ is the blocking group, wherein the blocking group is selected from the group consisting of —CH$_2$N$_3$, —NH$_2$, —CH$_2$CH═CH$_2$, —CH$_2$OCH$_3$, polyethylene glycol, and a substituted or unsubstituted alkyl.

8. A nucleotide moiety for one-color sequencing having the following formula:

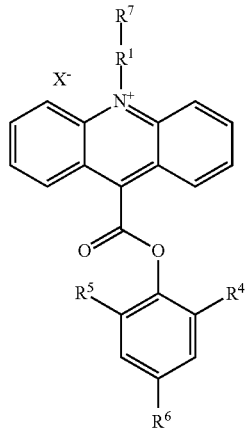

wherein:

R$^1$ is a linking group comprising a C$_1$-C$_8$alkyl sulfonyl piperidine;

R$^4$, R$^5$, and R$^6$ are each independently selected from the group consisting of hydrogen, —CH$_3$ and OCH$_3$;

R$^7$ is a nucleotide moiety of the following formula:

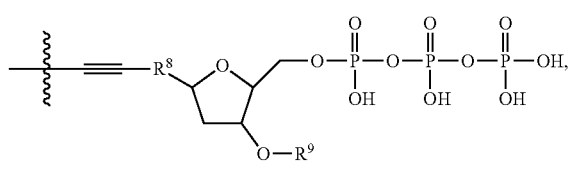

wherein
R⁸ is the nitrogenous base, which is a member selected from the group consisting of:
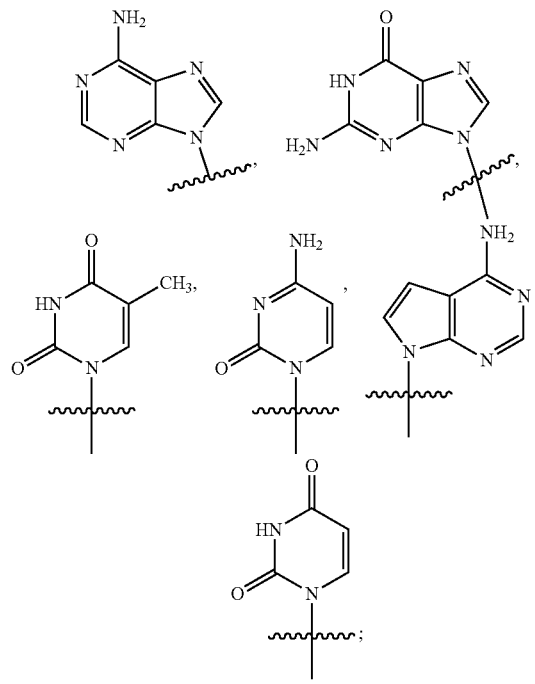
and
R⁹ is hydrogen or a blocking group; and
X⁻ is a counteranion.
9. The compound of claim 8, wherein the compound is a member selected from the group consisting of:
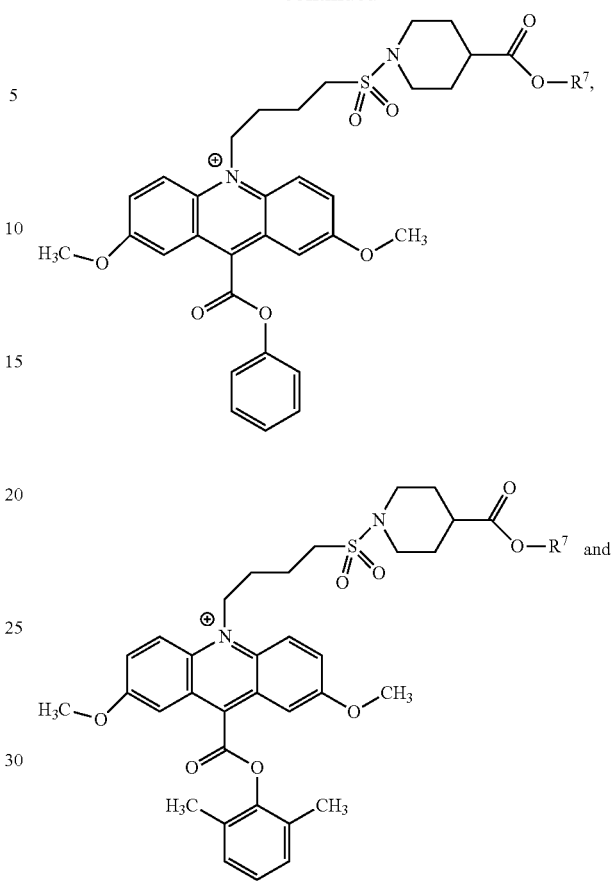
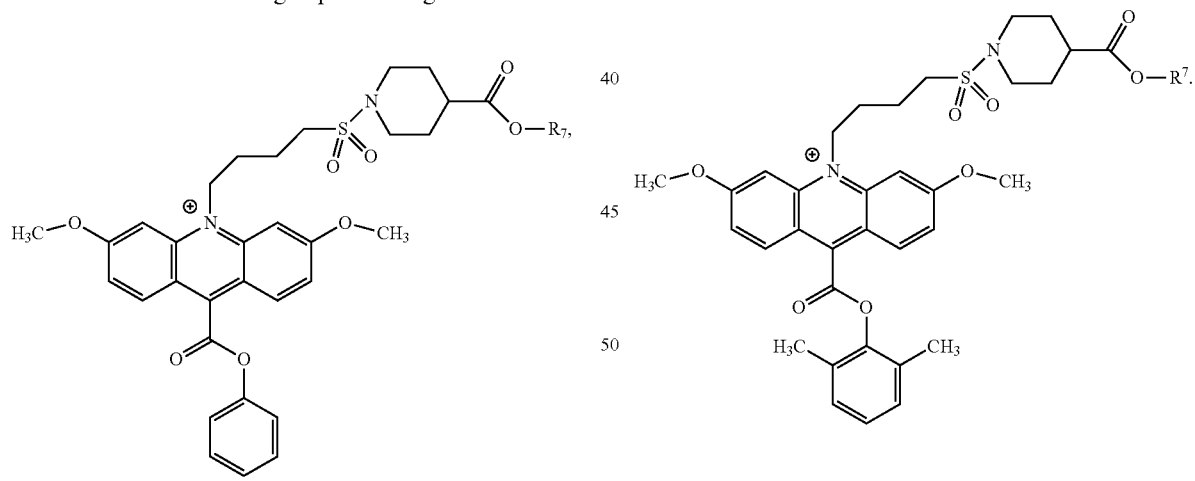
* * * * *